US010152805B2

(12) United States Patent
Hagiwara

(10) Patent No.: US 10,152,805 B2
(45) Date of Patent: Dec. 11, 2018

(54) IMAGE PROCESSING METHOD, IMAGE PROCESSING APPARATUS AND RADIATION TOMOGRAPHIC IMAGING APPARATUS, AND PROGRAM

(71) Applicant: General Electric Company, Schenectady, NY (US)

(72) Inventor: Akira Hagiwara, Tokyo (JP)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 66 days.

(21) Appl. No.: 15/246,398

(22) Filed: Aug. 24, 2016

(65) Prior Publication Data
US 2017/0061653 A1 Mar. 2, 2017

(30) Foreign Application Priority Data

Aug. 31, 2015 (JP) .................. 2015-170107

(51) Int. Cl.
G06K 9/00 (2006.01)
G06T 11/00 (2006.01)
A61B 6/03 (2006.01)
A61B 6/00 (2006.01)

(52) U.S. Cl.
CPC ............ G06T 11/005 (2013.01); A61B 6/032 (2013.01); A61B 6/5205 (2013.01); A61B 6/5258 (2013.01)

(58) Field of Classification Search
CPC ............................................ G06T 2207/20048
See application file for complete search history.

(56) References Cited

U.S. PATENT DOCUMENTS

| 4,729,100 A | 3/1988 | Tsujii | |
|---|---|---|---|
| 2005/0018889 A1* | 1/2005 | Li | G06T 5/002 382/128 |
| 2008/0118128 A1* | 5/2008 | Toth | G06T 11/003 382/131 |

(Continued)

FOREIGN PATENT DOCUMENTS

| JP | 6156946 A | 3/1986 |
|---|---|---|
| JP | 2000005159 A | 1/2000 |

(Continued)

OTHER PUBLICATIONS

Unofficial English Translation of Japanese Search Report issued in connection with corresponding JP Application No. 2015170107 dated Jun. 7, 2017.

(Continued)

Primary Examiner — Oneal R Mistry
(74) Attorney, Agent, or Firm — Fletcher Yoder, P.C.

(57) ABSTRACT

To reduce streak-like artifacts more in a radiation tomographic image: There is provided an image producing apparatus comprising: a processing component configured to, in scan data acquired by a radiation CT scan, apply suppression processing with which noise components are suppressed to a high noise level portion having a radiation detection level lower than a specified threshold, and apply enhancement processing with which noise components are enhanced to a low noise level portion having a radiation detection level equal to or higher than the specified threshold; and a reconstructing component configured to reconstruct an image based on the scan data subjected to the processing by the processing component.

20 Claims, 13 Drawing Sheets

(56) References Cited

U.S. PATENT DOCUMENTS

| | | | | |
|---|---|---|---|---|
| 2008/0232665 A1* | 9/2008 | Borsdorf | ............... | G06T 5/10 |
| | | | | 382/131 |
| 2009/0016482 A1* | 1/2009 | Shechter | ............... | A61B 6/032 |
| | | | | 378/4 |
| 2011/0116594 A1* | 5/2011 | Yamakawa | ............ | A61B 6/032 |
| | | | | 378/19 |
| 2013/0094739 A1* | 4/2013 | Okabe | ............... | A61B 6/032 |
| | | | | 382/131 |

FOREIGN PATENT DOCUMENTS

| | | | |
|---|---|---|---|
| JP | 2001273495 A | 10/2001 | |
| JP | 2013027520 A | 2/2013 | |

OTHER PUBLICATIONS

Unofficial English Translation of Japanese Office Action issued in connection with corresponding JP Application No. 2015170107 dated Jul. 4, 2017.

Unofficial English Translation of Japanese Preliminary Rejection for corresponding JP application No. 2015-170107 dated Jan. 16, 2018; 2 pages.

\* cited by examiner (a)

(b)

Fine Streak is reduced

IMAGE PROCESSING METHOD, IMAGE PROCESSING APPARATUS AND RADIATION TOMOGRAPHIC IMAGING APPARATUS, AND PROGRAM

CROSS-REFERENCE TO RELATED APPLICATIONS

This application claims priority to Japanese Priority Application 2015-170107, entitled "Image Processing Method, Image Processing Apparatus and Radiation Tomographic Imaging Apparatus, and Program", filed on Aug. 31, 2015 and listing Akira Hagiwara as sole inventor, which is herein incorporated by reference in its entirety for all purposes.

FIELD OF THE INVENTION

The present invention relates to an improvement technique for processing of reducing streak artifacts in a radiation tomographic image.

BACKGROUND

Streak artifacts are known as one type of artifacts appearing in radiation tomographic images. Moreover, one type of the most representative streak artifacts is fine streak artifacts. The fine streak artifacts are a group of subtle linear artifacts generated in a specific direction and at a specific location.

Generation of fine streak artifacts is caused by the non-uniform geometry of a human body, and it is believed that one cause thereof is non-uniformity of the noise level across view angles or across detector channels in collected scan data.

In the prior art, there have been proposed a variety of techniques for suppressing such fine streak artifacts. One of the most general techniques is one directed to improvement of non-uniformity of the noise level by applying smoothing processing or the like to a portion of scan data in which the radiation detection level is low and the noise level is relatively high because of a long radiation penetration path and high radiation attenuation to reduce the noise level.

SUMMARY OF THE INVENTION

Problem to be Solved by the Invention

Smoothing processing on scan data, however, cannot fully suppress fine streak artifacts as a result of limitations of the degree of smoothing due to a concomitant side effect that sharpness of a reconstructed image is degraded.

Under such circumstances, there is a need for a technique capable of reducing streak artifacts more in a radiation tomographic image.

Means for Solving the Problem

The invention, in its first aspect, provides an image producing method causing a computer to execute:

a processing step of, in scan data acquired by a radiation CT (Computed Tomography) scan, applying suppression processing with which noise components are suppressed to a high noise level portion having a radiation detection level lower than a specified threshold, and applying enhancement processing with which noise components are enhanced to a low noise level portion having a radiation detection level equal to or higher than said specified threshold; and a reconstructing step of reconstructing an image based on the scan data subjected to the processing by said processing step.

The invention, in its second aspect, provides an image producing apparatus comprising:

processing means for, in scan data acquired by a radiation CT scan, applying suppression processing with which noise components are suppressed to a high noise level portion having a radiation detection level lower than a specified threshold, and applying enhancement processing with which noise components are enhanced to a low noise level portion having a radiation detection level equal to or higher than said specified threshold; and reconstructing means for reconstructing an image based on the scan data subjected to the processing by said processing means.

The invention, in its third aspect, provides the image producing apparatus as described regarding the second aspect above, wherein:

said processing means enhances the degree of said suppression processing as said radiation detection level becomes lower in said high noise level portion.

The invention, in its fourth aspect, provides the image producing apparatus as described regarding the second or third aspect above, wherein:

said processing means enhances the degree of said enhancement processing as said radiation detection level becomes higher in said low noise level portion.

The invention, in its fifth aspect, provides the image producing apparatus as described regarding any one of the second through fourth aspects above, wherein:

said scan data is radiation detector data before logarithmic transformation.

The invention, in its sixth aspect, provides the image producing apparatus as described regarding any one of the second through fourth aspects above, wherein:

said scan data is projection data after logarithmic transformation.

The invention, in its seventh aspect, provides the image producing apparatus as described regarding any one of the second through sixth aspects above, wherein:

said scan data is data corresponding to one view.

The invention, in its eighth aspect, provides the image producing apparatus as described regarding any one of the second through seventh aspects above, wherein:

said suppression processing is processing employing a smoothing filter.

The invention, in its ninth aspect, provides the image producing apparatus as described regarding any one of the second through eighth aspects above, wherein:

said enhancement processing is processing employing a sharpening filter.

The invention, in its tenth aspect, provides the image producing apparatus as described regarding any one of the second through eighth aspects above, wherein:

said enhancement processing is processing of adding noise components.

The invention, in its eleventh aspect, provides the image producing apparatus as described regarding any one of the second through tenth aspects above, wherein:

said specified threshold is adjusted based on a result of analysis on said image.

The invention, in its twelfth aspect, provides the image producing apparatus as described regarding any one of the second through eleventh aspects above, wherein:

said radiation is X-rays.

The invention, in its thirteenth aspect, provides the image producing apparatus as described regarding any one of the second through twelfth aspects above, wherein:

said radiation CT scan is achieved by rotating around an object to be imaged a radiation source and a radiation detector in which a plurality of detector elements are arranged, driving said radiation source to emit radiation onto said object to be imaged, and detecting by said radiation detector radiation passing through said object to be imaged.

The invention, in its fourteenth aspect, provides a radiation tomographic imaging apparatus comprising: the image producing apparatus as described regarding any one of the second through thirteenth aspects above.

The invention, in its fifteenth aspect, provides a program for causing a computer to function as the means in the image producing apparatus as described regarding any one of the second through thirteenth aspects.

Effect of the Invention

According to the invention in the aspects described above, in scan data, suppression processing is applied to a high noise level portion having a radiation detection level lower than a specified threshold, and enhancement processing is applied to a low noise level portion having a radiation detection level equal to or higher than the threshold. Thus, by lowering the noise level in a portion having a high noise level, and in addition, actively enhancing it on the contrary in a portion having a low noise level, making uniform of the noise level may be promoted as compared with conventional techniques, and streak artifacts based on non-uniformity of the noise level may be reduced more.

MODES FOR CARRYING OUT THE INVENTION

Now an embodiment of the invention will be described hereinbelow. It should be noted that the invention is not hereby limited.

Figure 1:
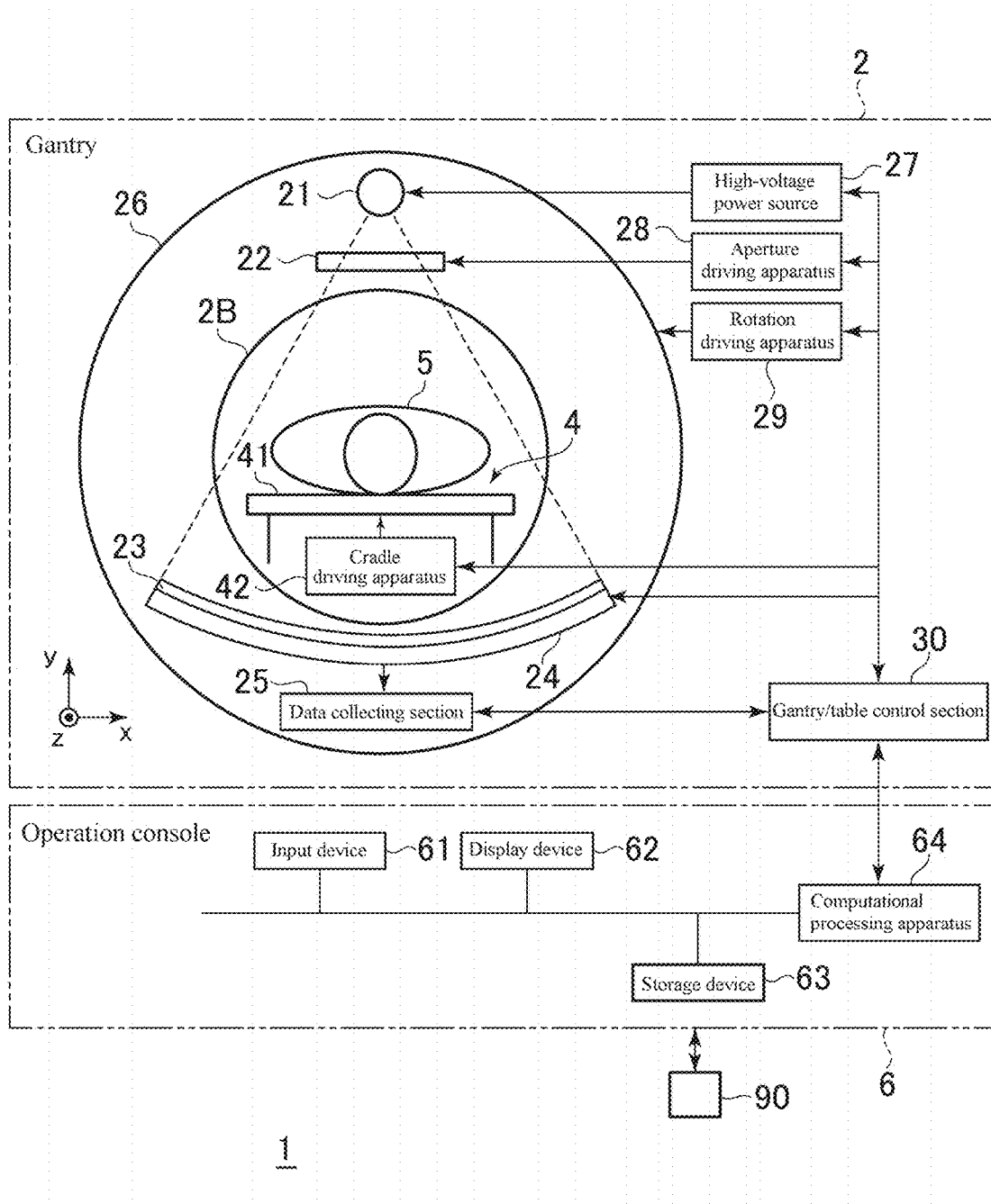
FIG. 1 A diagram schematically showing a hardware configuration of an X-ray CT apparatus in an embodiment of the invention.

FIG. 1 is a diagram schematically showing a hardware configuration of an X-ray CT apparatus (X-ray Computed Tomography system) in accordance with the present embodiment.

As shown in FIG. 1, the X-ray CT apparatus 1 comprises a gantry 2, an imaging table 4, and an operation console 6.

The gantry 2 has an X-ray tube 21, an aperture 22, a collimator device 23, an X-ray detector 24, a data collecting section 25, a rotating section 26, a high-voltage power source 27, an aperture driving apparatus 28, a rotation driving apparatus 29, and a gantry/table control section 30.

The X-ray tube 21 and X-ray detector 24 are disposed to face each other across a bore 2B.

The aperture 22 is disposed between the X-ray tube 21 and bore 2B. It shapes X-rays emitted from the X-ray tube 21 at its X-ray focus toward the X-ray detector 24 into a fan beam or a cone beam.

The collimator device 23 is disposed between the bore 2B and X-ray detector 24. The collimator device 23 removes scatter rays that would otherwise enter the X-ray detector 24.

The X-ray detector 24 has a plurality of X-ray detector elements two-dimensionally arranged in a direction of the span (referred to as channel direction) and a direction of the thickness (referred to as row direction) of the fan-shaped X-ray beam emitted from the X-ray tube 21. Each respective X-ray detector element detects X-rays passing through a subject 5 laid in the bore 2B, and outputs an electric signal depending upon the intensity thereof. The subject 5 is an animate being, such as, for example, a human or an animal.

The data collecting section 25 receives the electric signal output from each X-ray detector element in the X-ray detector 24, and converts it into X-ray data for collection.

The rotating section 26 is rotatably supported around the bore 2B. The rotating section 26 has the X-ray tube 21, aperture 22, collimator device 23, X-ray detector 24, and data collecting section 25 mounted thereon.

The imaging table 4 has a cradle 41 and a cradle driving apparatus 42. The subject 5 is laid on the cradle 41. The cradle driving apparatus 42 moves the cradle 41 into/out of the bore 2B, i.e., an imaging volume, in the gantry 2.

The high-voltage power source 27 supplies high voltage and current to the X-ray tube 21.

The aperture driving apparatus 28 drives the aperture 22 and modifies the shape of its opening.

The rotation driving apparatus 29 rotationally drives the rotating section 26.

The gantry/table control section 30 controls several apparatuses and sections in the gantry 2, the imaging table 4, and the like.

The operation console 6 accepts several kinds of operation from an operator. The operation console 6 has an input device 61, a display device 62, a storage device 63, and a computational processing apparatus 64. In the present embodiment, the operation console 6 is constructed from a computer.

As shown in FIG. 1, a direction of the body axis of the subject 5, i.e., a direction of transportation of the subject 5 by the imaging table 4, will be referred to herein as z-direction. Moreover, a vertical direction will be referred to as y-direction, and a horizontal direction orthogonal to the y- and z-directions as x-direction.

Next, a function of the X-ray CT apparatus in accordance with the present embodiment will be described. The X-ray CT apparatus in accordance with the present embodiment has a correcting function capable of reducing fine streak artifacts more that could not be fully reduced by conventional streak artifact reducing processing.

Figure 2:
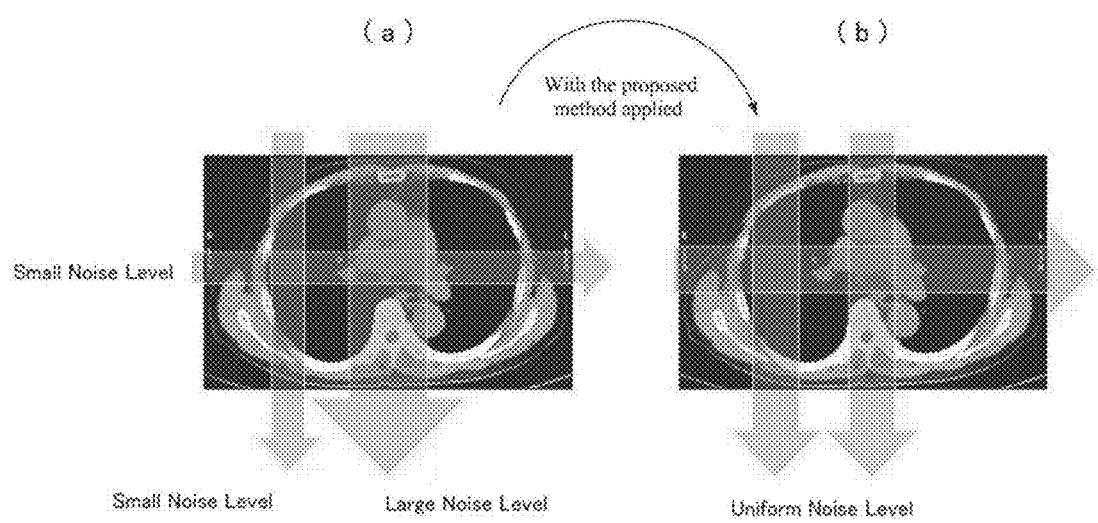
FIG. 2 A diagram showing the concept of a method of correcting fine streak artifacts in accordance with the present proposal.

FIG. 2 shows the concept of a method of correcting fine streak artifacts in accordance with the present proposal. The noise level found in scan data depends upon a length (penetration length) over which X-rays travel through the subject. A reason thereof is that for a longer penetration length, more X-ray photons are lost on the way of penetration and noise increases relative to the amount of the photons, which thereby raises the noise level. As shown in FIG. 2(a) [left], a human body contains a heart region or a spine, which is a strong X-ray absorber, in its cross-sectional plane in a central vertical direction (anterior-posterior direction, or AP direction), and accordingly, the penetration length is longer and the noise level is higher. On the other hand, a position of the human body passing through a lung field region in the vertical direction does not contain the spine, which is a strong X-ray absorber, and the lung field is largely the air, so that the substantial penetration length is shorter and the noise level is lower than in the central vertical direction. Similarly, a position passing through the lung field in a horizontal direction (right-left direction) does not contain the spine, which is a strong X-ray absorber, although it contains the heart region, and accordingly, the penetration length is shorter and the noise level is lower than in the central vertical direction.

It is an object of the method proposed herein to make the noise level described above uniform at any position and in any direction, as shown in FIG. 2(b) [right].

Figure 3:
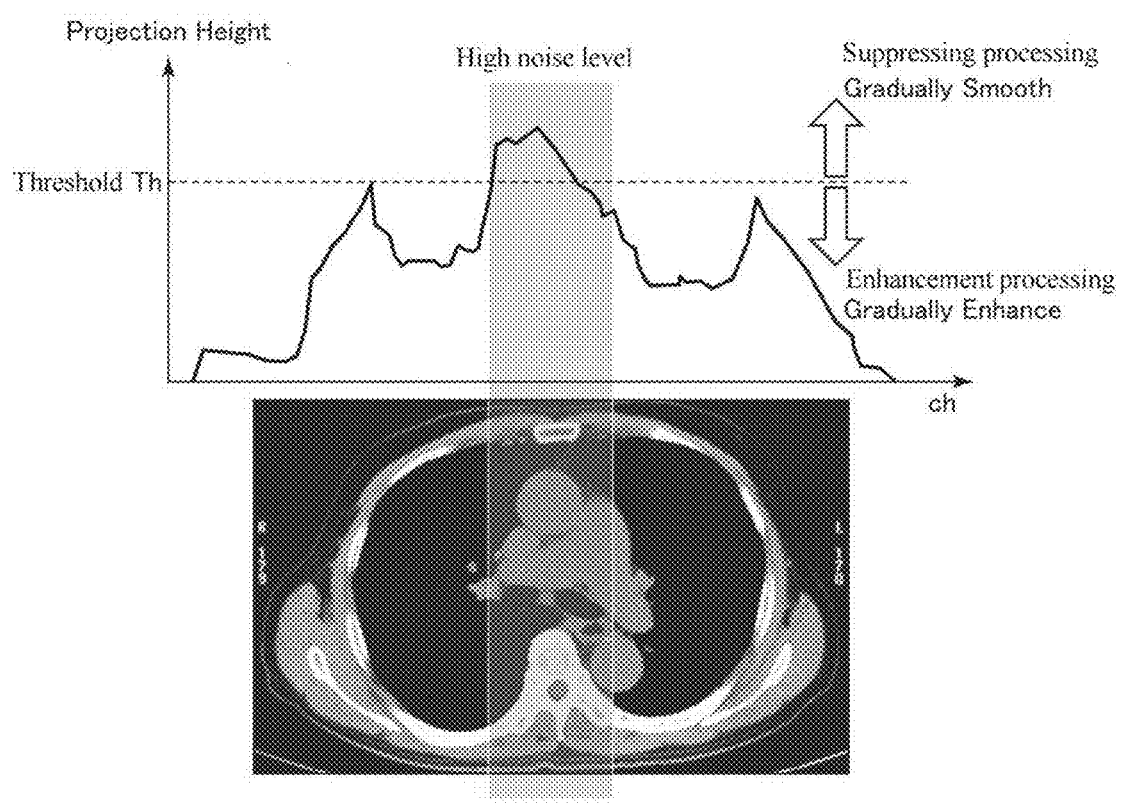
FIG. 3 A diagram showing the continuation of the concept of the method of correcting fine streak artifacts in accordance with the present proposal.

FIG. 3 shows the continuation of the concept of the method of correcting fine streak artifacts in accordance with the present proposal. While the appropriate times at which correction processing should be performed may include several ones with respect to what is generally called pre-processing and back-projection processing, they are generally classified as two times. One of them is in the earlier half of the processing, which applies to a case that processing is performed at a stage when the scan data expresses the amount of counts of X-ray photons. The other is in the later half of the processing, which applies to a case that processing is performed at a stage when the scan data expresses projection data (projection) after temporal/spatial normalization has been applied. In the latter case, times before and after logarithmic transformation may be optionally selected.

Referring to FIG. 3, there is shown an exemplary case in which processing is applied to projection data obtained by pre-processing including logarithmic transformation. The fundamental concept is as follows: a portion of scan data having an X-ray detection level lower than a specified threshold, i.e., a high noise level portion having a data value (wave height) of projection data exceeding a threshold, is subjected to suppression processing. On the other hand, a portion of the scan data having an X-ray detection level equal to or higher than the threshold, i.e., a low noise level portion having a data value (wave height) of the projection data equal to or smaller than the threshold, is subjected to enhancement processing. More preferably, the degree of the suppression processing is enhanced for a higher noise level, while the degree of the enhancement processing is enhanced for a lower noise level. Thus, by lowering the noise level in a portion having a high noise level, and in addition, actively enhancing it on the contrary in a portion having a low noise level, making uniform of the noise level may be promoted as compared with conventional techniques, and streak artifacts based on non-uniformity of the noise level may be reduced more.

Suppression processing on scan data normally exerts its suppressing effect not only on noise components but also on non-noise components, thus lowering the sharpness in a reconstructed image. Accordingly, there are limitations to the degree of suppression processing that may be applied. Moreover, since a higher noise level detrimentally affects image quality of a reconstructed image by nature, no thought is given to application of processing of increasing the noise level. Then, in general, it may be contemplated to make the noise level uniform by applying suppression processing to a portion having a high noise level, as in the prior art. In this case, however, the noise level in a portion having a low noise level from the beginning cannot be reached, and perfect making uniform of the noise level may be sometimes difficult.

However, the effect of reducing fine streak artifacts due to promoted making uniform of the noise level often achieves a greater merit depending upon the degree of the noise level considering the detrimental effect due to enhancement of the noise level. From such a point of view, the method proposed herein may be considered to be a technique of high inventive value.

Figure 4:
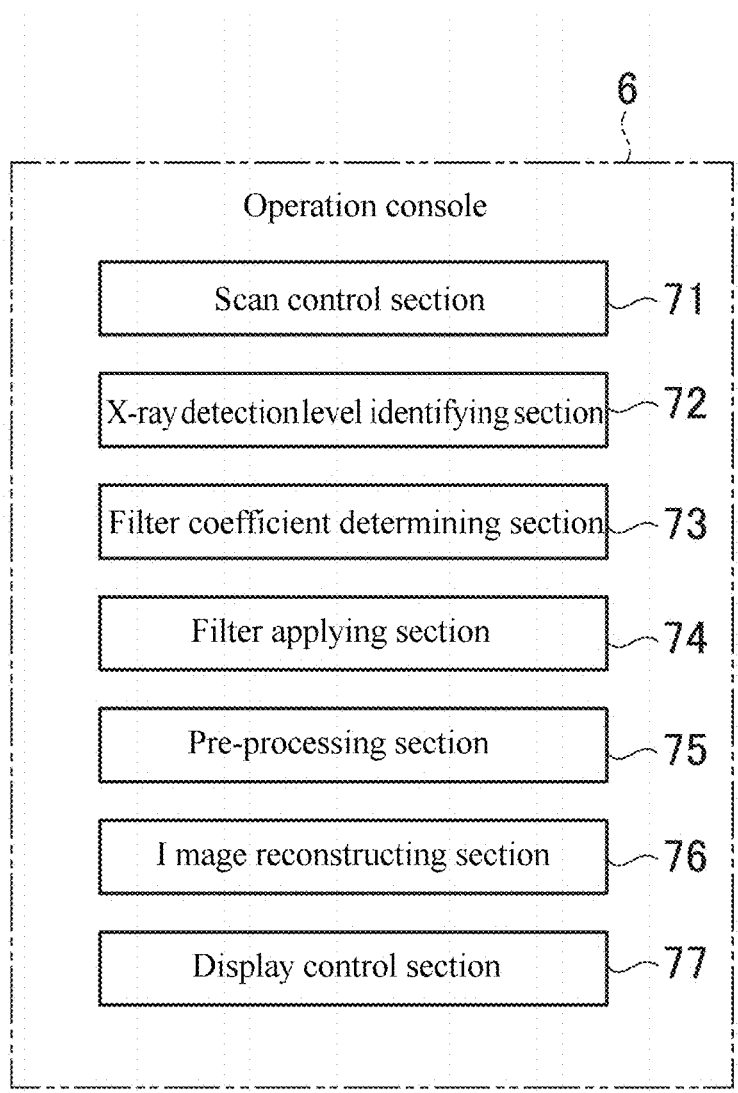
FIG. 4 A functional block diagram of an operation console in the X-ray CT apparatus in accordance with the present embodiment.

FIG. 4 is a functional block diagram of the operation console in the X-ray CT apparatus in accordance with the present embodiment.

The operation console 6 in the X-ray CT apparatus in accordance with the present embodiment has a scan control section 71, an X-ray detection level identifying section 72, a filter coefficient determining section 73, a filter applying section 74, a pre-processing section 75, an image reconstructing section 76, and a display control section 77 as functional blocks for implementing the functions described above.

The X-ray detection level identifying section 72, filter coefficient determining section 73, filter applying section 74, and pre-processing section 75 represent an example of the processing means in the invention. The image reconstructing section 76 represents an example of the reconstructing means in the invention.

The operation console 6 functions as these functional blocks by the computational processing apparatus 64 executing specified programs. The specified programs are stored in the storage device 63, or an externally connected storage device or medium 90, for example.

The scan control section 71 controls the gantry/table control section 30 so that a scan is performed in response to an operation by the operator.

The X-ray detection level identifying section 72 identifies an X-ray detection level on a channel data-by-channel data basis in scan data acquired by a scan. The X-ray detection level is a level depending upon the intensity of X-rays detected or the number of counts of photons counted by a detector element, where the X-ray detection level rises as the intensity of X-rays or the number of counts of photons increases. In other words, the X-ray detection level is lower for a longer X-ray penetration length through the imaged object or for higher X-ray attenuation, while it is higher for a shorter X-ray penetration length through the imaged object or for lower X-ray attenuation.

The filter coefficient determining section 73 determines coefficients for a filter depending upon the identified X-ray detection level.

The filter applying section 74 applies the filter with the determined coefficients to radiation detector data or projection data.

The pre-processing section 75 applies pre-processing including logarithmic transformation to radiation detector data to obtain projection data.

The image reconstructing section 76 reconstructs a tomographic image based on the projection data.

The display control section 77 controls the display device 62 to display the reconstructed tomographic image on its screen.

Next, the flow of processing in the X-ray CT apparatus in accordance with the present embodiment will be described.

Figure 5:
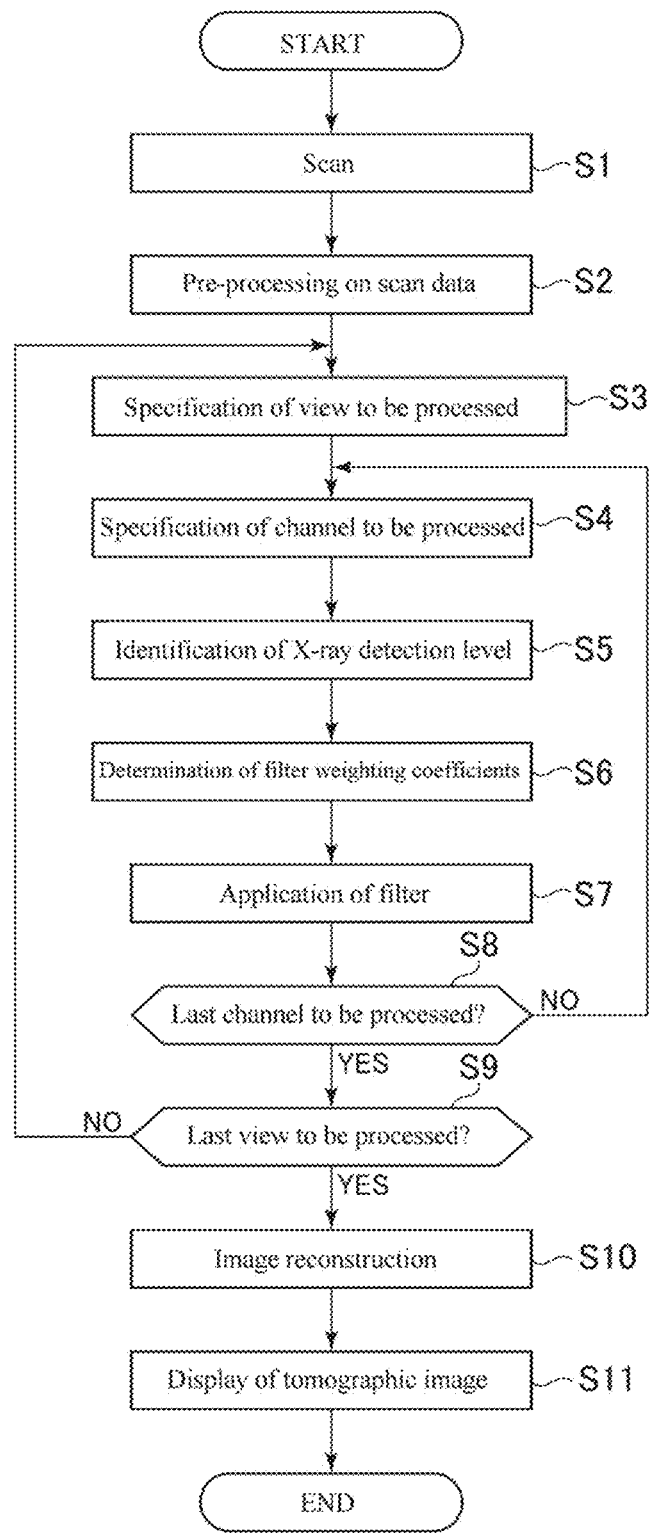
FIG. 5 A flow chart showing the flow of processing in the X-ray CT apparatus in accordance with the present embodiment.

FIG. 5 is a flow chart showing the flow of processing in the X-ray CT apparatus in accordance with the present embodiment.

At Step S1, a scan is performed. Specifically, the scan control section 71 controls the gantry/table control section 30 to perform a scan on a body part to be imaged 5h, which is an object to be imaged, in the subject.

Figure 6:
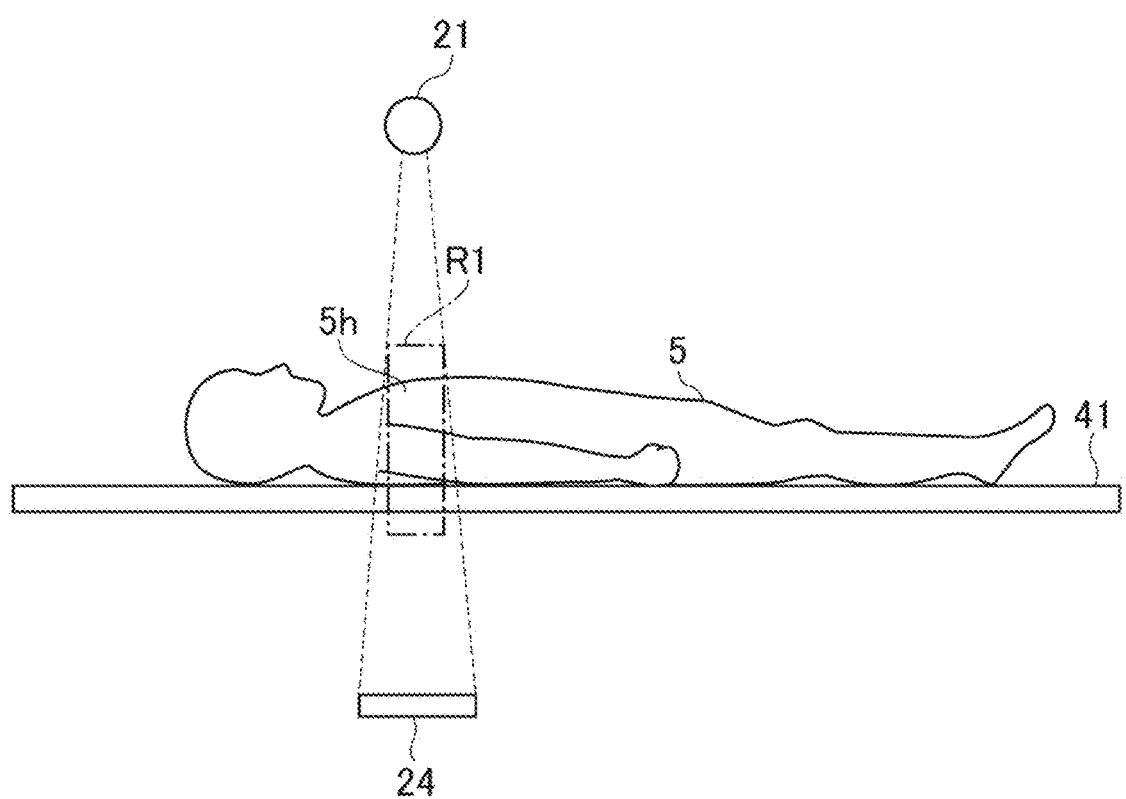
FIG. 6 A diagram showing a situation in which a body part to be imaged in a subject is scanned in the present embodiment.

FIG. 6 is a diagram schematically showing a situation in which the body part to be imaged 5h in the subject is scanned in the present embodiment. In the present example, a scan is performed on an imaging volume R1 containing the body part to be imaged 5h in the subject 5 laid on the cradle 41, as shown in FIG. 6. The scan is achieved by emitting X-rays from the X-ray tube 21 at its X-ray focus onto the subject 5 while rotating the X-ray tube 21 and X-ray detector 24 around the subject 5. The scan is a what is generally called half scan, wherein the view angular range is 180 degrees plus the fan angle α of the X-ray beam. Once the scan has been performed, X-ray detector data in a plurality of views are collected. X-ray detector data D in one view has channel data $D_{i,j}$ for each X-ray detector element depending upon the output value thereof. Channel data corresponding to an X-ray path whose X-ray penetration length is long and X-ray attenuation is high causes the output of the X-ray detector element to lower, resulting in a low X-ray detection level.

At Step S2, pre-processing on the X-ray detector data is performed. Specifically, the pre-processing section 75 applies pre-processing including logarithmic transformation processing to the collected X-ray detector data D in a plurality of views to provide projection data I in the plurality of views.

The following equation is an exemplary calculation formula representing the pre-processing:

$$I = \mu l = \log\left(\frac{D_0}{D}\right) = \log D_0 - \log D \quad (1\text{-}1)$$

where l is a penetration path length, μ is an X-ray absorption coefficient, $D_0$ is an X-ray air data value, and D is an X-ray detector data value.

At Step S3, a view to be processed is specified. Specifically, the X-ray detection level identifying section 72 specifies a view of the projection data to be processed.

At Step S4, a channel to be processed is specified. Specifically, the X-ray detection level identifying section 72 specifies a channel for the channel data to be processed.

At Step S5, an X-ray detection level is identified. Specifically, the X-ray detection level identifying section 72 identifies the X-ray detection level for data in the specified view and channel. Since the object to be processed is projection data after logarithmic transformation here, the data value (wave height) of the projection data is identified as an indication representing the X-ray detection level, and it is considered that the X-ray detection level decreases for a greater data value, while it increases for a smaller data value.

At Step S6, weighting coefficients for a filter are determined. Specifically, the filter coefficient determining section 73 determines weighting coefficients for the filter to be applied to the data to be processed depending upon the X-ray detection level identified at Step S5.

An exemplary calculation formula for the filter is given by the following equation:

$$I'_{i,j} = \sum_{m=-M}^{M} W_{i,m} I_{i+m,j} \quad (2\text{-}1)$$

$$W = (w_1, w_2, w_3, w_2, w_1) \quad (2\text{-}2)$$
$$w_3 = 1 - 2 \times (w_1 + w_2)$$
$$M = 2$$

$$w_1 = \begin{cases} w_{init11}, & \text{if } I_{i,j} > Th2 \\ w_{init11} \times \left(\frac{I_{i,j} - Th1}{Th2 - Th1}\right)^{n1}, & \text{if } I_{i,j} > Th1, I_{i,j} < Th2 \\ w_{init12} \times \left(\frac{I_{i,j} - Th1}{Th1}\right)^{n2}, & \text{if } I_{i,j} > 0, I_{i,j} < Th1 \\ -w_{init12}, & \text{if } I_{i,j} < 0 \end{cases} \quad (2\text{-}3)$$

$$w_2 = \begin{cases} w_{init21}, & \text{if } I_{i,j} > Th2 \\ w_{init21} \times \left(\frac{I_{i,j} - Th1}{Th2 - Th1}\right)^{n1}, & \text{if } I_{i,j} > Th1, I_{i,j} < Th2 \\ w_{init22} \times \left(\frac{I_{i,j} - Th1}{Th1}\right)^{n2}, & \text{if } I_{i,j} > 0, I_{i,j} < Th1 \\ -w_{init22}, & \text{if } I_{i,j} < 0 \end{cases} \quad (2\text{-}4)$$

$$\text{For example } \begin{array}{l} 0 < w_{init11} \leq 0.1, \quad 0 < w_{init12} \leq 0.05 \\ 0 < w_{init21} \leq 0.2, \quad 0 < w_{init22} \leq 0.1 \end{array} \quad (2\text{-}5)$$

where $I_{i,j}$ is a data value corresponding to a detector element at a channel index i and a row index j, W is a set of weighting coefficients, n1 and n2 are arbitrary constants, Th1 is a first threshold, and Th2 is a second threshold.

Figure 7:
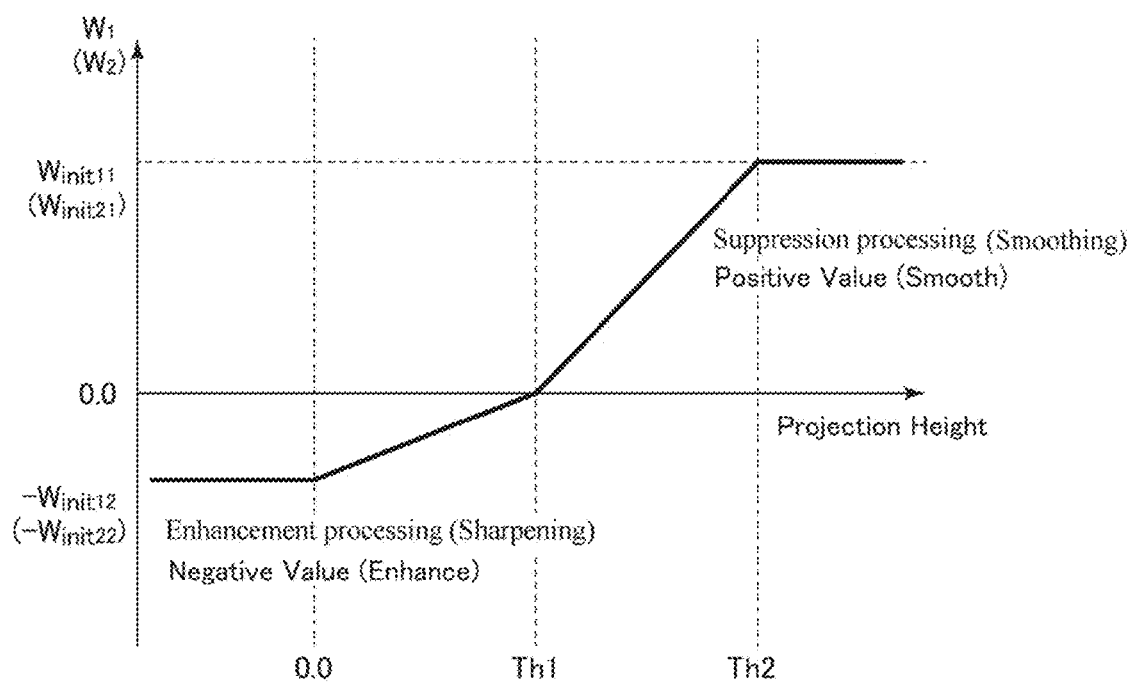
FIG. 7 A diagram showing an exemplary relationship between a data value of projection data and weighting coefficients for a filter.

FIG. 7 shows an exemplary relationship between the data value (wave height) in projection data and weighting coefficients for the filter. The weighting coefficients for the filter are determined based on the relationship.

In the present example, when the data value I in the projection data is equal to or greater than the first threshold Th1, a first weighting coefficient w1 and a second weighting coefficient w2 for the filter both take positive values, and a third weighting coefficient w3 also takes a positive value. That is, the filter to be applied is a smoothing filter, whose filter processing is suppression processing with which noise components are suppressed. Moreover, the first weighting coefficient w1 and second weighting coefficient w2 are larger for a greater data value I of the projection data and the degree of suppression processing is enhanced, although they reach a maximum and no longer increase when the data value I is equal to or greater than the second threshold Th2.

On the other hand, when the data value I in the projection data is smaller than the first threshold Th1, the first weighting coefficient w1 and second weighting coefficient w2 for the filter both take negative values, whereas the third weighting coefficient w3 takes a positive value. That is, the filter to be applied is a sharpening filter, whose filter processing is enhancement processing with which noise components are enhanced. Moreover, the first weighting coefficient w1 and second weighting coefficient w2 are smaller for a smaller data value I of the projection data and the degree of enhancement processing is enhanced, although they reach a minimum and no longer decrease when the data value I is zero or smaller.

In other words, such a filter has a function as follows: When the data value I is smaller than the first threshold Th1, the data is regarded as that in a low noise level portion having a high X-ray detection level, so that enhancement processing is applied to the data. On the other hand, when the data value I is equal to or greater than the first threshold Th1, the data is regarded as that in a high noise level portion having a low X-ray detection level, so that suppression processing is applied to the data. The degree of the enhancement or suppression processing is then adjusted according to the X-ray detection level for the data. Thus, the noise level in data for the channels is made uniform with high accuracy.

It should be noted that the first threshold Th1, the second threshold Th2, the range of change of the first weighting coefficient w1 and second weighting coefficient w2, the rate of change (gradient) thereof with respect to the data value, and the like are appropriately determined from an empirical rule or from a result of a simulation.

At Step S7, the filter is applied. Specifically, the filter applying section 74 applies the filter with the coefficients determined at Step S6 to the data to be processed to achieve suppression processing or enhancement processing.

At Step S8, a decision is made as to whether the channel being processed is a last one. Specifically, the X-ray detection level identifying section 72 decides whether the channel for the channel data being processed is a last one in the projection data in the view being processed. In the case that it is the last one, the process goes to a next step. In the case that it is not, the process goes back to Step S4, where the channel is updated and the processing is continued.

At Step S9, a decision is made as to whether the view being processed is a last one. Specifically, the X-ray detection level identifying section 72 decides whether the view for the projection data being processed is a last one in the projection data in the plurality of views. In the case that it is the last one, the process goes to a next step. In the case that it is not, the process goes back to Step S3, where the view is updated and the processing is continued.

At Step S10, image reconstruction is performed. Specifically, the image reconstructing section 76 reconstructs a tomographic image based on the filtered projection data.

At Step S11, the tomographic image is displayed. Specifically, the display control section 77 controls the display device 62 to display the tomographic image reconstructed at Step S9 on its screen.

Subsequently, examples of application of the method proposed herein will be demonstrated.

Figure 8:
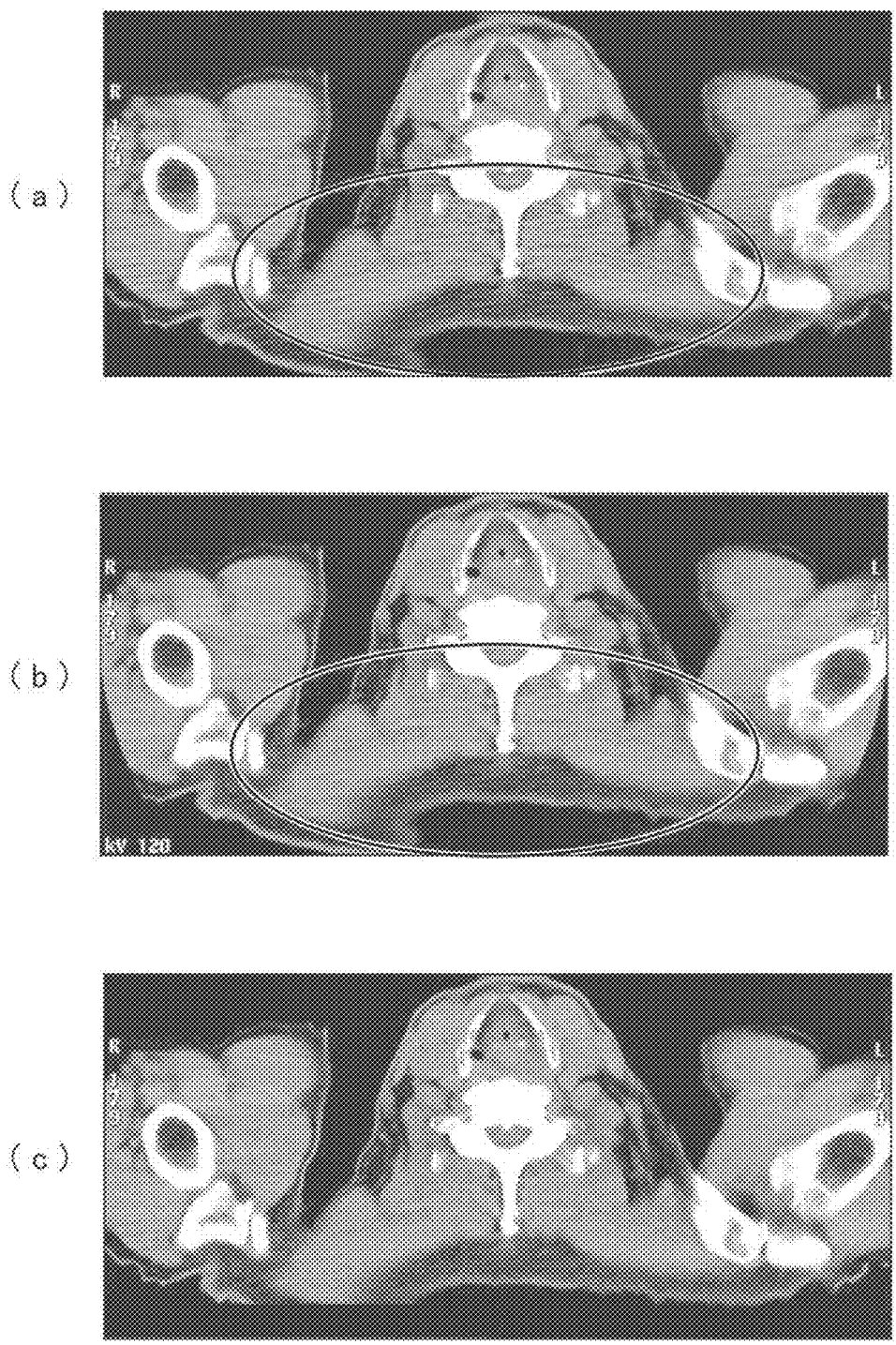
FIG. 8 An illustration showing a first example of application of the method proposed herein.

FIG. 8 shows a first example of application of the method proposed herein. The illustration includes clinical images of an actual shoulder joint region. In FIG. 8, (a) [upper] is an uncorrected image, (b) [central] is an image with correction by a conventional technique, i.e., correction in which suppression processing is applied to a high noise level portion, (c) [lower] is an image by the method proposed herein. In the uncorrected image, strong fine streak artifacts are observed between the left and right shoulder joints. In the image by the conventional technique, making uniform of the noise level is partial, and therefore, it can be seen that reduction of fine streak artifacts having directional and positional dependency is limited. Moreover, there arises a side effect that fine streak artifacts are more conspicuous on the contrary because of reduced background image noise. On the other hand, in the image of the method proposed herein, the effect of fine streak artifact reduction is more recognizable than the conventional technique because making uniform of the noise level is attempted regardless of the angle or position. Moreover, it can be seen that spatial resolution of the image of the method proposed herein is improved as compared with the other images.

Figure 9:
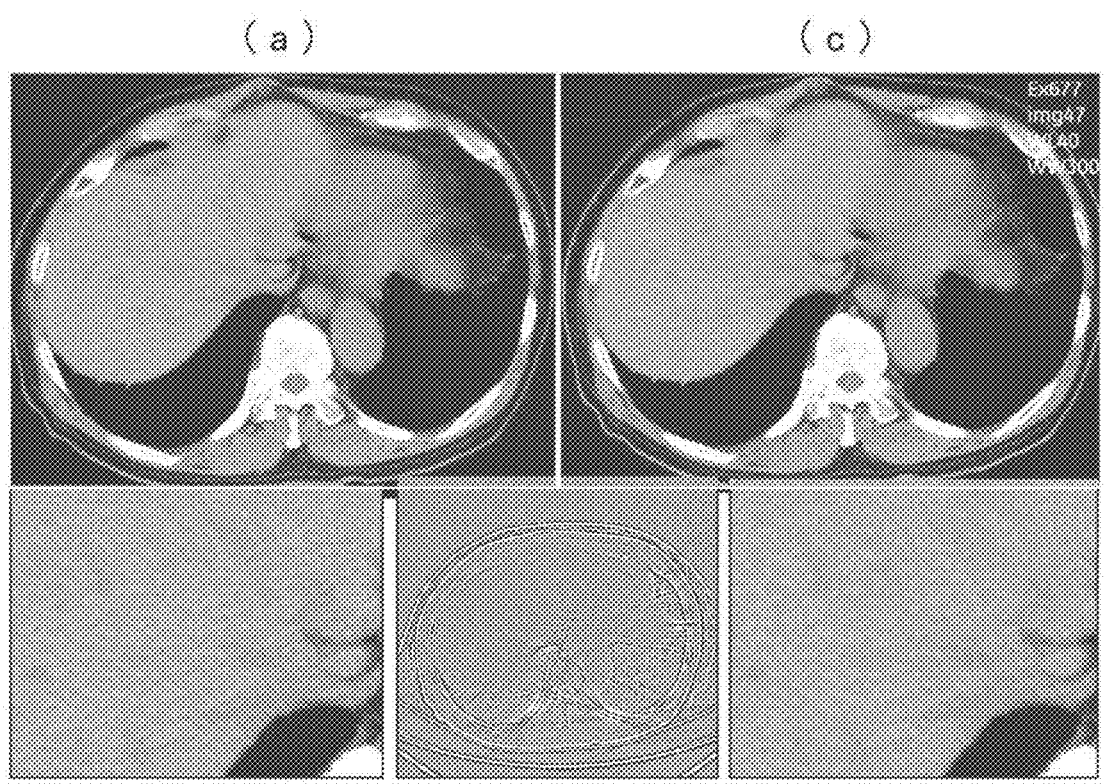
FIG. 9 An illustration showing a second example of application of the method proposed herein.

FIG. 9 shows a second example of application of the method proposed herein. The illustration includes clinical images of an actual liver region. In FIG. 9, (a) [upper left] is an uncorrected image, (b) [lower left] is a partial enlarged view of the uncorrected image, (c) [upper right] is an image by the method proposed herein, and (d) [lower right] is a partial enlarged view of the image by the method proposed herein. Moreover, FIG. 9(e) [lower central] is an image representing a difference between pre- and post-application of the method proposed herein. In the uncorrected image, fine streak artifacts from the spine are observed within the liver. From the subtraction image, directionally and positionally characteristic fine streak artifacts can be seen. That is, it can be understood that image quality is significantly improved by the effect of fine streak artifact reduction by the method proposed herein. Moreover, the image by the method proposed herein has better spatial resolution than the other images.

Figure 10:
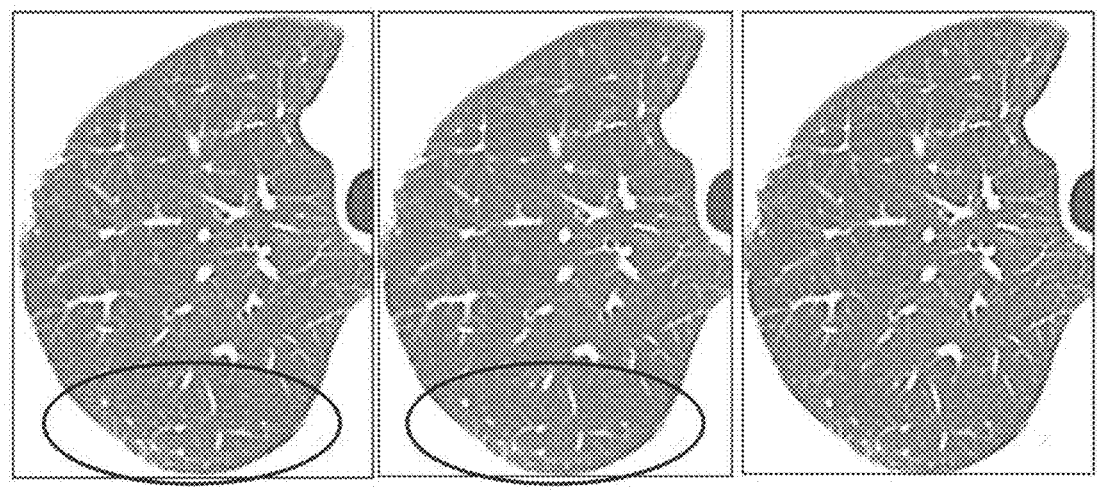
FIG. 10 An illustration showing a third example of application of the method proposed herein.

FIG. 10 shows a third example of application of the method proposed herein. The illustration includes clinical images of an actual lung field region. In FIG. 10, (a) [left] is an uncorrected image, (b) [central] is an image by the conventional technique, and (c) [right] is an image by the method proposed herein. In the uncorrected image, fine streak artifacts generated in the spinal direction are observed in a lower portion of the lung field region. Since suppression processing is basically performed in the conventional technique, the fine streak artifacts are reduced, although reduction in spatial resolution is found at the same time. On the other hand, since suppression processing and enhancement processing are performed in combination in the method proposed herein, enhancement processing is dominant in the lung field region having a generally short penetration length, thus improving spatial resolution in the lung field region.

Figure 11:
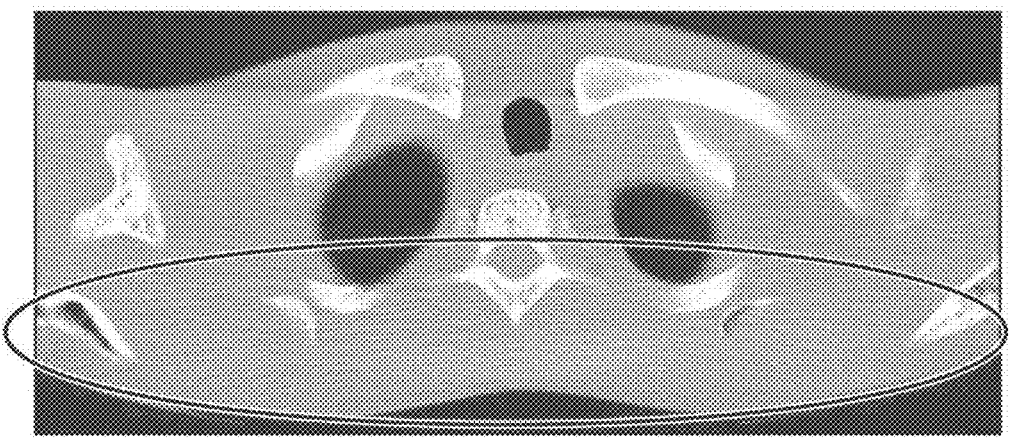
FIG. 11 An illustration showing a fourth example of application of the method proposed herein.
Figure 11:
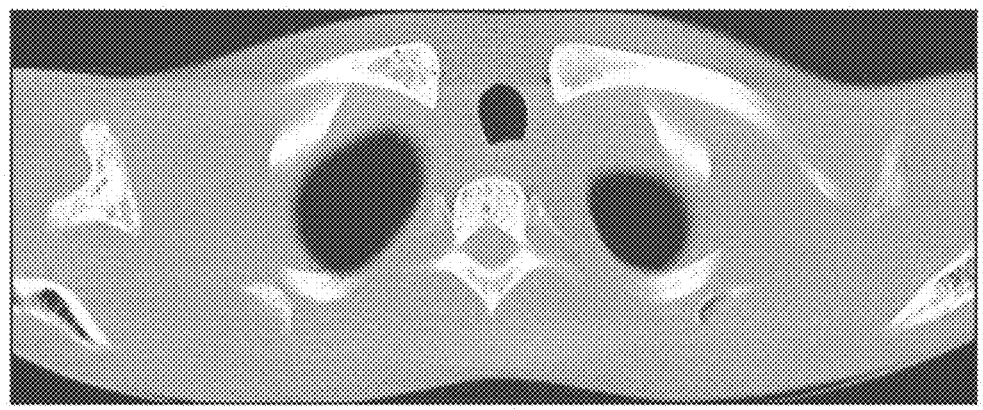

FIG. 11 shows a fourth example of application of the method proposed herein. The illustration includes images of a phantom simulating a human body. In FIG. 11, (a) [upper] is an uncorrected image, and (b) [lower] is an image by the method proposed herein. In the uncorrected image, rather strong fine streak artifacts are observed in a generally horizontal direction. From the image by the method proposed herein, a great effect of fine streak artifact reduction may be observed. Moreover, the image of the method proposed herein has better spatial resolution than the other image.

Figure 12:
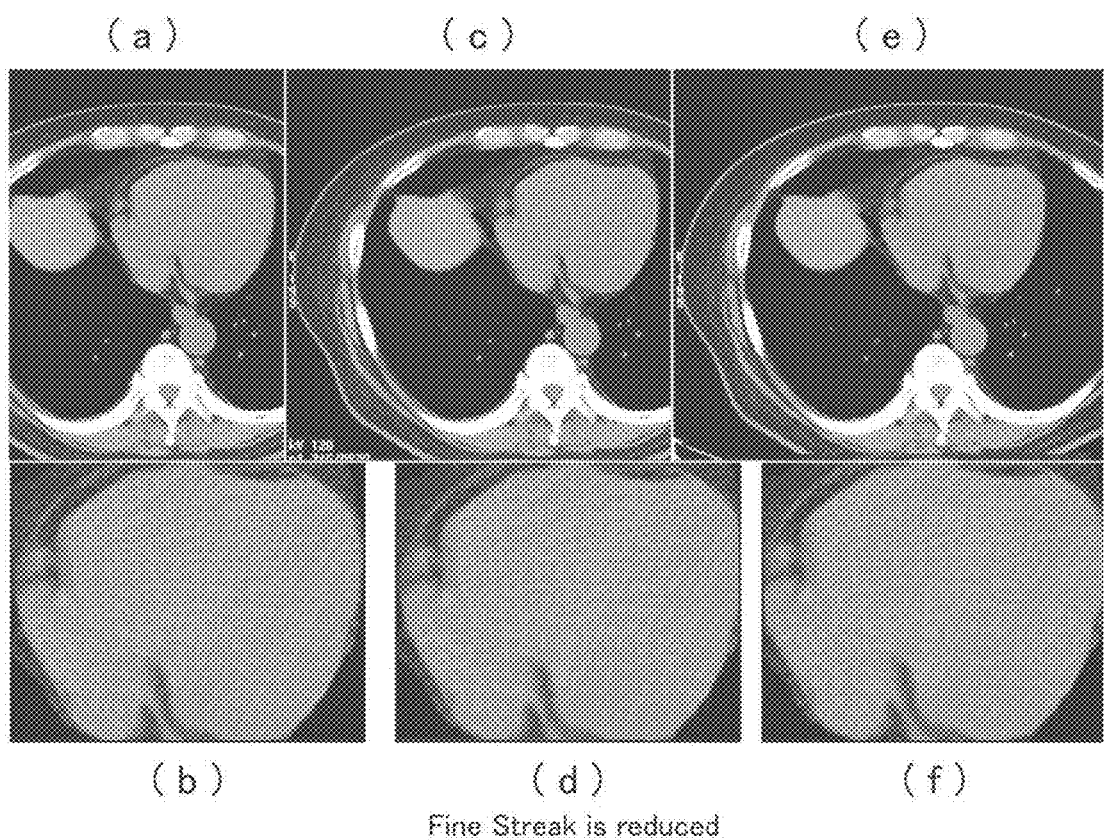
FIG. 12 An illustration showing a fifth example of application of the method proposed herein.

FIG. 12 shows a fifth example of application of the method proposed herein. The illustration includes clinical images of an actual heart region. In FIG. 12, (a) [upper left] is an uncorrected image, (b) [lower left] is a partial enlarged view of the uncorrected image, (c) [upper central] is an image by the conventional technique, (d) [lower central] is a partial enlarged view of the image by the conventional technique, (e) [upper right] is an image by the method proposed herein, and (0 [lower right] is a partial enlarged view of the image by the method proposed herein. In the uncorrected image, fine streak artifacts from the spine are found within the heart. In the image by the method proposed herein, it can be seen that the fine streak artifacts are reduced very well. The image also has good spatial resolution.

Now uniformity of the noise level in the z-direction will be studied.

Figure 13:
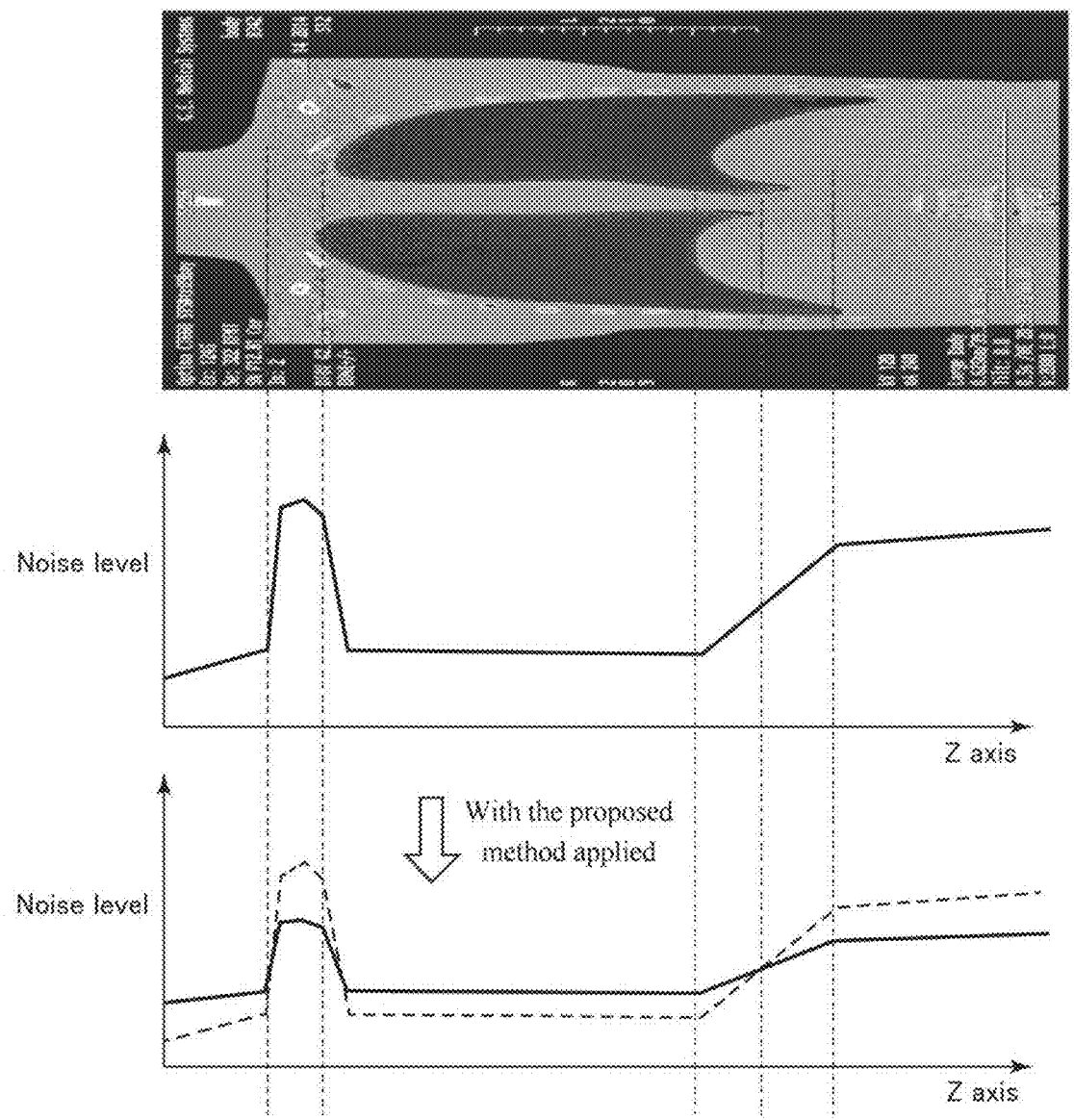
FIG. 13 An illustration for explaining study on uniformity of the noise level in the z-direction.

FIG. 13 is a diagram for explaining this study. In general, the amount of attenuation of X-ray photons is small in a location having a short penetration length in a human body, and consequently noise in a reconstructed image tends to be low. On the contrary, the amount of attenuation of X-ray photons is large in a location having a long penetration length in a human body, and consequently image noise tends to be high. Accordingly, for a non-uniform structure such as a human body, image noise is rather low in the lung field region while it is rather high in the abdominal region, resulting in non-uniformity of the image noise level in the z-direction i.e., in a body-axis direction.

On the other hand, the method proposed herein raises the noise level in the lung field region in a human body because it operates as enhancement processing in the lung field region in which the penetration length is short, whereas it lowers the noise level in the abdominal region because it operates as suppression processing in the abdominal region in which the penetration length is long. Accordingly, the method proposed herein is effective also in improvement of non-uniformity of the image noise level in the body-axis direction as described above.

Thus, according to the present embodiment, in scan data, suppression processing is applied to a high noise level portion having a radiation detection level lower than a specified threshold, and enhancement processing is applied to a low noise level portion having a radiation detection level equal to or higher than the threshold. Thus, by lowering the noise level in a portion having a high noise level, and in addition, enhancing it on the contrary in a portion having a low noise level, making uniform of the noise level may be promoted as compared with conventional techniques, and fine streak artifacts based on non-uniformity of the noise level may be reduced more. Moreover, in this embodiment, there is almost no degradation of spatial resolution in spite of the fact that fine streak artifacts are reduced.

Furthermore, in this embodiment, the degree of the suppression processing is enhanced for a higher noise level, while the degree of the enhancement processing is enhanced for a lower noise level. Thus, making uniform of the noise level may be promoted with higher accuracy, and the effect of fine streak artifact reduction may be further improved.

It should be noted that the invention is not limited to the embodiment described above, and several modification may be made within the scope not departing from the spirit of the invention.

For example, while in this embodiment, the first threshold Th1 is fixed, it may be automatically adjusted based on projection data or on a result of analysis on a reconstructed image so that the noise level in scan data is more uniform.

Moreover, for example, while in this embodiment, enhancement processing is applied to a low noise level portion in scan data to raise the noise level, it may be raised by applying processing that simply adds noise. In this case, again, making uniform of the noise level is promoted, and therefore, the effect of fine streak artifact reduction may be expected.

Furthermore, while the present embodiment is an X-ray CT apparatus, the invention is also applicable to a tomographic imaging apparatus using radiation other than X-rays, for example, that using gamma rays.

In addition, a program for causing a computer to function as several means for performing control and/or processing in the X-ray CT apparatus described above and a recording medium in which such a program is stored each represent an exemplary embodiment of the invention as well.

The invention claimed is:

1. An image producing method causing a computer to execute:
   a processing step of, in scan data acquired by a radiation CT scan, applying suppression processing to suppress noise components of a high noise level portion having a radiation detection level lower than a specified threshold, and applying enhancement processing to enhance noise components of a low noise level portion having a radiation detection level equal to or higher than the specified threshold; and
   a reconstructing step of reconstructing an image based on the scan data subjected to the processing by the processing step.

2. The image producing method of claim 1, comprising a displaying step of displaying the image on a display.

3. An image producing apparatus comprising:
   a processing component configured to, in scan data acquired by a radiation CT scan, apply suppression processing to suppress noise components of a high noise level portion having a radiation detection level lower than a specified threshold, and apply enhancement processing to enhance noise components of a low noise level portion having a radiation detection level equal to or higher than the specified threshold; and
   a reconstructing component configured to reconstruct an image based on the scan data subjected to the processing by the processing component.

4. The image producing apparatus as recited in claim 3, wherein the processing component enhances the degree of the suppression processing as the radiation detection level becomes lower in the high noise level portion.

5. The image producing apparatus as recited in claim 3, wherein the processing component enhances the degree of the enhancement processing as the radiation detection level becomes higher in the low noise level portion.

6. The image producing apparatus as recited in claim 3, wherein the scan data is radiation detector data before logarithmic transformation.

7. The image producing apparatus as recited in claim 3, wherein the scan data is projection data after logarithmic transformation.

8. The image producing apparatus as recited in claim 3, wherein the scan data is data corresponding to one view.

9. The image producing apparatus as recited in claim 3, wherein the suppression processing is processing employing a smoothing filter.

10. The image producing apparatus as recited in claim 3, wherein the enhancement processing is processing employing a sharpening filter.

11. The image producing apparatus as recited in claim 3, wherein the enhancement processing is processing of adding noise components.

12. The image producing apparatus as recited in claim 3, wherein the specified threshold is adjusted based on a result of analysis on the image.

13. The image producing apparatus as recited in claim 3, wherein the radiation is X-rays.

14. The image producing apparatus as recited in claim 3, wherein the radiation CT scan is achieved by rotating around an object to be imaged a radiation source and a radiation detector in which a plurality of detector elements are arranged, driving the radiation source to emit radiation onto the object to be imaged, and detecting by the radiation detector radiation passing through the object to be imaged.

15. The image producing apparatus of claim 3, comprising a display configured to display the image.

16. A radiation tomographic imaging apparatus comprising:
- an X-ray source configured to emit X-rays;
- an X-ray detector facing the X-ray source and configured to generate signals in response to X-rays incident on the X-ray detector; and
- an operation console, comprising:
  - a processing component configured to, in scan data acquired by a radiation CT scan, apply suppression processing to suppress noise components of a high noise level portion having a radiation detection level lower than a specified threshold, and apply enhancement processing to enhance noise components of a low noise level portion having a radiation detection level equal to or higher than the specified threshold; and
  - a reconstructing component configured to reconstruct an image based on the scan data subjected to the processing by the processing component.

17. The radiation tomographic imaging apparatus of claim 16, wherein the processing component enhances the degree of the suppression processing as the radiation detection level becomes lower in the high noise level portion.

18. The radiation tomographic imaging apparatus of claim 16, wherein the processing component enhances the degree of the enhancement processing as the radiation detection level becomes higher in the low noise level portion.

19. The radiation tomographic imaging apparatus of claim 16, wherein the scan data is radiation detector data before logarithmic transformation.

20. The radiation tomographic imaging apparatus of claim 16, wherein the scan data is projection data after logarithmic transformation.

* * * * *